United States Patent [19]

Fujita et al.

[11] Patent Number: 5,484,700
[45] Date of Patent: Jan. 16, 1996

[54] METHOD FOR ASSAYING NUCLEIC ACIDS USING NAPHTHOL DERIVATIVE PHOSPHATE

[75] Inventors: Satoshi Fujita; Naoto Kagiyama; Masayoshi Momiyama, all of Sapporo, Japan

[73] Assignee: Aisin Seiki Kabushiki Kaisha, Kariya, Japan

[21] Appl. No.: 806,189

[22] Filed: Dec. 13, 1991

[30] Foreign Application Priority Data

Dec. 21, 1990 [JP] Japan ................................. 2-413201

[51] Int. Cl.$^6$ ................. C12Q 1/68; C12Q 1/42
[52] U.S. Cl. ................. 435/6; 435/21; 534/573; 548/113; 558/9; 558/193
[58] Field of Search ............ 435/6, 7.71, 7.72, 435/21; 534/573; 548/113; 558/9, 193; 436/35, 501, 800

[56] References Cited

U.S. PATENT DOCUMENTS

| | | | |
|---|---|---|---|
| 3,140,283 | 7/1964 | Depoorter | 548/119 |
| 3,180,873 | 4/1965 | Schmidt | 260/313 |
| 4,582,789 | 4/1986 | Sheldon, III et al. | 436/6 |

FOREIGN PATENT DOCUMENTS 4041880  7/1991  Germany .

OTHER PUBLICATIONS

Vaughan A., Fluorometric Methods for Analysis . . . , Anal Chem 43 (6) May 1971 pp. 721–724.
West S., A Multiple Staining Procedure for the Detection . . . , Anal Chem 190, 1990, pp. 254–258.

*Primary Examiner*—William H. Beisner
*Assistant Examiner*—Ralph Gitomer
*Attorney, Agent, or Firm*—Finnegan, Henderson, Farabow, Garrett & Dunner

[57] ABSTRACT

Methods for detecting nucleic acids in a sample, using naphthol derivative phosphates, are provided. Nucleic acids present in a sample are contacted with phosphatase, producing a modified phosphatase. A naphthol derivative phosphate is contacted with the modified phosphatase to produce a reaction product. Any reaction product formed is detected by irradiating it with an excited light and detecting a fluorescence emitted from the reaction product. Naphthol derivative phosphates useful in these methods are also provided. Methods for production of naphthol derivative phosphates are also provided.

7 Claims, 1 Drawing Sheet

Pg : $10^{-12}$g

Pg : $10^{-12}$g

METHOD FOR ASSAYING NUCLEIC ACIDS USING NAPHTHOL DERIVATIVE PHOSPHATE

BACKGROUND OF THE INVENTION

1. Field of Invention

The present invention relates to a method for assaying nucleic acids which can efficiently detect nucleic acids, etc. by fluorescence.

2. Related Art

In medical and biological fields, a means for labeling, for example, a DNA (or RNA) probe with a radioactive isotope, hybridizing the labeled probe with a target nucleic acid and then detecting the target nucleic acid by autoradiography has been currently performed widely.

However, the isotope method involves many drawbacks which are serious obstacles to application and development of this technology.

The drawbacks of the isotope method are as follows.

(a) In nucleic acid hybridization, the isotope method lacks any spatial resolution sufficient to reveal relative positional relationship between contiguous signal.

(b) Experimental procedures using isotopes can only be carried out in isotope laboratories equipped with special facilities. This is a cause for hindering application of the hybridization method especially to clinical inspection.

(c) Use of isotope is dangerous for laboratory workers even in laboratories. In addition, a danger for ordinary people also always exists because of wastes, etc.

(d) A long time (several weeks to several months) may be required for detection, so application to rapid clinical diagnostics is difficult.

(e) Radioactivity decays with a definite half-life period so that experiments should be scheduled to fit a purchase date of the isotope. If the schedule chart is slightly altered, there would be a danger of wasting isotope or experimental results in a large scale.

(f) In order to enhance detect ion sensitivity, it is required to incorporate radioactivity to the nucleic acid probe as high as possible. However, the nucleic acid labeled enough to increase its radioactivity easily suffers from radioactive disintegration.

(g) In general, isotope is extremely expensive and it is not unusual to use isotope worth several hundred yen in one run. This prevents general spread of the hybridization method.

In view of such background, some DNA or RNA labeling methods in place of radioactive isotope have been developed so far. For example, BLU GENE KIT commercially available from Bethesda Research Laboratories Inc. (BRL Inc.) is known. Furthermore, "Nucleic acid probe and use thereof" is disclosed in Japanese Patent Application Laid-Open No. 60-226888.

However, these techniques merely eliminate a part of the drawbacks described above. In particular, detection sensitivity is not comparable to that of the isotope method.

In view of such problems, an object of the present invention is to provide a method for assaying nucleic acids which solves the drawbacks of safety precautions, etc. in the isotope method and provides excellent detection sensitivity.

SUMMARY OF THE INVENTION

The present invention provides a method for assaying nucleic acids or the like which comprises binding phosphatase to a sample such as nucleic acids, etc., reacting the phosphatase with a naphthol derivative phosphate, then irradiating the reaction products with an excited light and detecting fluorescence emitting therefrom.

DETAILED DESCRIPTION OF PREFERRED EMBODIMENTS

Figure 1:
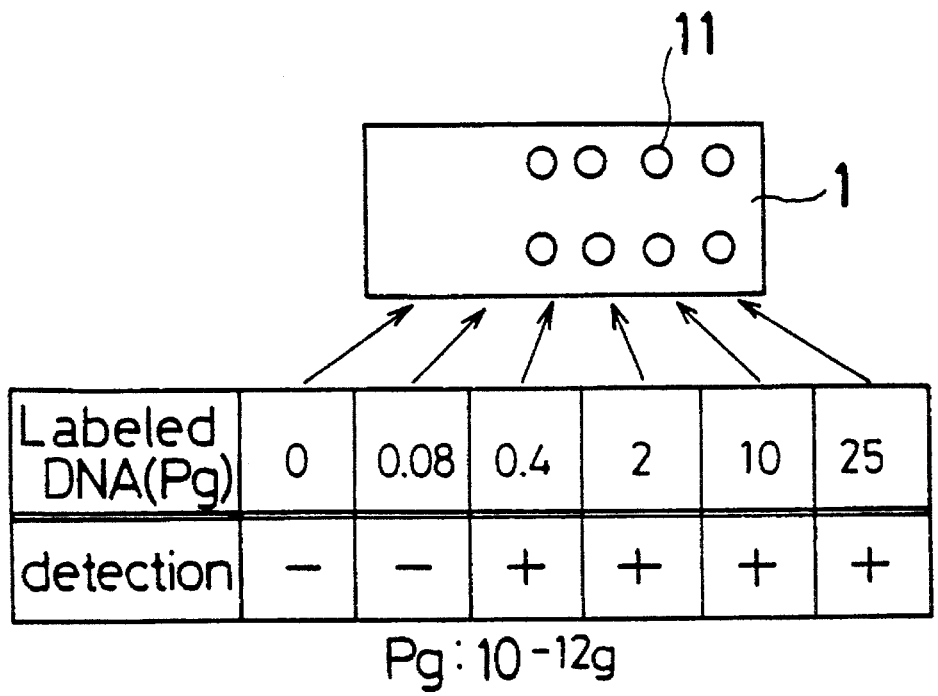
FIG. 1 is the test results detected in Example 1.

Examples of the phosphatase include alkali phosphatase acid phosphatase, etc.

The detection of a sample in the present invention includes detection of nucleic acid (DNA or RNA), detection of protein, immunological detection of a chemical compound using antibody, etc.

An example of the phosphatase fluorescence substance wherein a naphtol derivative phosphate used in a method for assaying is represented the formula $P\text{-Nap-R}_{(n)}$.

In the formula described above, Nap represents a naphthalene, P represents a phosphate combined with said naphthalene, $R_{(n)}$ represents a substitution combined with said naphthalene.

In the formula described above, $P\text{-Nap-R}_{(n)}$ is represented by the following formula 1 or 2:

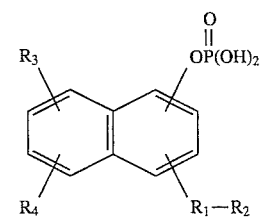

Formula 1

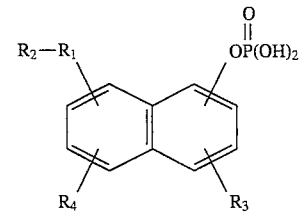

In the formula 1 or 2 described above, $R_1$ represents amide, vinyl, alkyl which C are 1~3, ester, or is represented by the following formula 3:

Formula 3

(In the formula 3 described above, X represents alkoxide, phenoxide), and $R_2$ represents aryl, condensing aromatic, thio-aryl, alkyl, alkoxide, phenoxide, and $R_3$, $R_4$ are the same or different, and represents hydrogen, halogen, alkyl, alkoxide, phenoxide, aminoacetyl, cyano, ester.

In the formula 1 or 2 described above, $R_2$ is aryl and represented by the following formula 4:

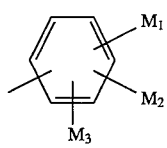

Formula 4

In the formula 4 described above, $M_1$, $M_2$, $M_3$ are the same different, and represent hydrogen, halogen, alkyl where C are 1~3, alkoxide, phenoxide, aminophenyl, benzyl, aminoacetyl, cyano, or represents by the following formula 5:

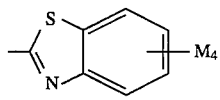

Formula 5

In the formula 5 described above, $M_4$ represents hydrogen, alkyl where C are 1~3, alkoxide, cyano, aminoacetyl.

In the formula 1 or 2 described above, if $R_2$ is condensation aromatic, $R_2$ is represented by the following formula 6, 7, or 8:

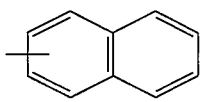

Formula 6

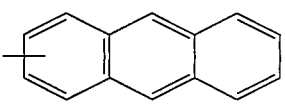

Formula 7

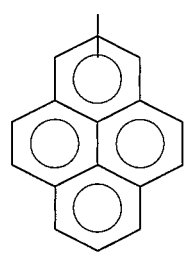

Formula 8

In the formula 1 or 2 described above, if $R_2$ is thioaryl, $R_2$ is represented by the following formula 9:

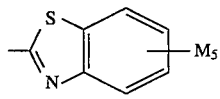

Formula 9

In the formula 9 described, $M_5$ represents hydrogen, alkyl where C is 1 or 2, alkoxide, cyano, aminoacetyl.

In the method for assay in accordance with the present invention, the naphthol derivative phosphate is reacted with the phosphatase described above followed by irradiating with an excited light, whereby the dephosphating product of the naphthol derivative phosphate emits fluorescence. Then, the emitted fluorescence can be detected.

The aforesaid naphthol derivative phosphate is reacted with the phosphatase combined with a sample (e.g. nucleic acids) on a membrane filter made of nylon so as to produce a dephosphating product of the naphthol derivative phosphate, which adheres to the nylon membrane filter and displays fluorescence. Then, fluorescence and the pattern thereof (spots, and bands produced by electrophoresis) are detected by irradiating with the excited light.

In the present invention, intense fluorescence can be obtained by the use of the naphthol derivative phosphate described above so that detection sensitivity can be improved; for example, $10^{-13}$ g of DNA is detectable.

In the present invention, no isotope is used and therefore, the drawbacks of the prior art can be removed.

Thus, according to the present invention, a method for assaying nucleic sensitivity can be presented.

Further, according to the method of the present invention, the dephosphating product of the naphthol derivative phosphate can be produced in high yield.

DESCRIPTION OF THE PREFERRED EMBODIMENTS

EXAMPLE 1

For the purpose of verifying the effect of the naphthol derivative phosphate as a probe for nucleic acids, DNA Labeling and Detection kit of Boehringer Mannheim, and 2-allyl[2'-(3,4-dimethylphenyl)]3-naphtol phosphate were used to detect DNA on a nylon membrane filter.

DNA was labeled with digoxigein (Dig), diluted and spotted on the nylon membrane filter. Each of the spots included DNA of herring spermatozoa in the amount of 50 ng ($50 \times 10^{-9}$ g) as DNA of no peculiarity.

The aforesaid experiment was conducted on 0.08 to 25 pg of Dig-labeled DNA as shown in FIG. 1. 0 pg in the Figure shows a blank test. The test results are shown in FIG. 1. Reference numeral 1 designates a carrier filter for a specimen of nucleic acids, and 11 designates fluorescence sensitized portions. "+" represents a fact that the DNA can be detected. "±" represents that the DNA cannot distinctly be detected. "−" represents that DNA cannot be detected. As apparent from the above, DNA could satisfactorily be detected even in the small amount of 0.4 pg.

Figure 2:
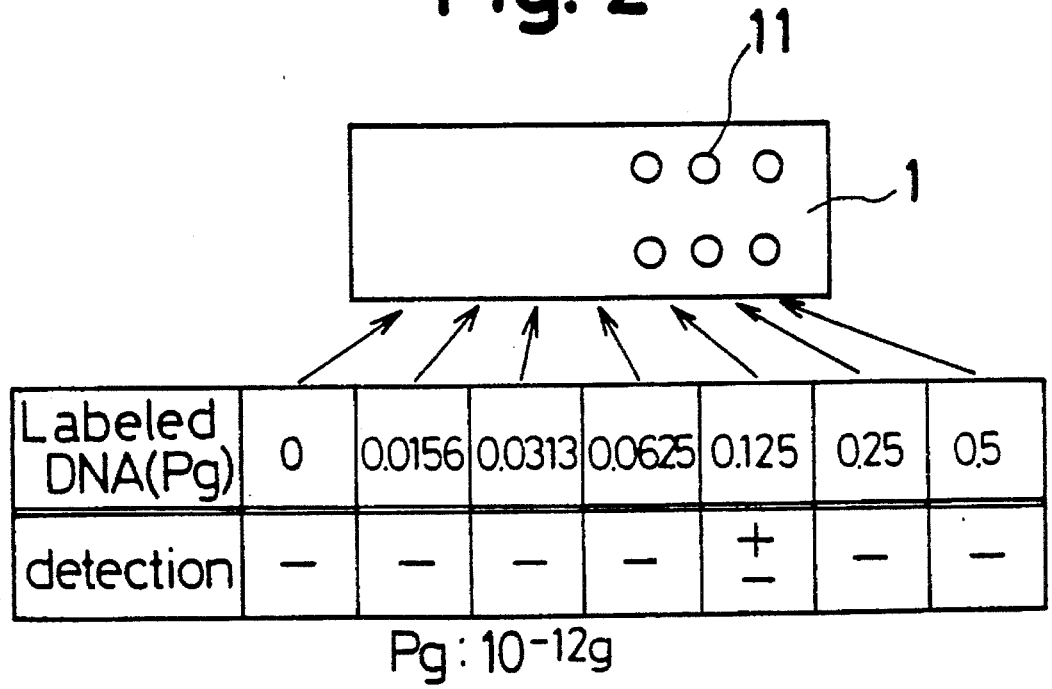
FIG. 2 is the test results detected in Example 1.

Then, using the smaller amount of the aforesaid DNA, another experiment was conducted on 0.0156 to 0.5 pg of Dig-labeled DNA, another experiment was conducted on 0.0156 to 0.5 pg of Dig-labeled DNA in the same manner as described above. The test results are shown in FIG. 2 similarly in FIG. 1. As shown in FIG. 2, satisfactory detection could be attained in the 0.0125 pg (125 fg). In the amount of 0.125 pg, detection was not satisfactory.

In this former experiment, a conventional color development detection using azo-color, Fast Blue BB (of POLYSCIENCE, INC.) was conducted. As the result of this detection, the detective spot included 0.5 pg ($0.5 \times 10^{-12}$ g) of the DNA.

A naphthol derivative phosphate of the present invention was produced by the following processes.

1 mol equivalent amount of 3,4-dimethylbenzylchloride and triphenylphosphine were mixtured, then the mixture was stirred at the room temperature for 10 minutes with no solvent. Next, the mixture was added with 7 ml of the xylene anhydride, then is stirred at the oil temperature 130° for 1 hour. When the crystal was formed, the reaction was terminated. The crystal was filtered by aspiration, and was washed with ether. Then the crystal was re-crystallized with acetonitrile anhydride to give the fall rate 40% of 3,4-dimethylbenzylphosphonium(A) shown by the following formula 10.

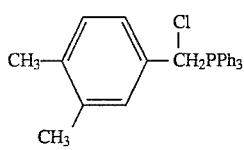

Formula 10

At the other hand, 9 ml of pyridine anhydride was added to 5 g of 1-hydroxy-2-naphtoaldehyde, and the mixture were stirred at 0° for 10 minutes, then the mixture was stirred with 2 mol of refined acetic anhydride at 0° C. for 1 hours, next at the room temperature for 2 hours. After reaction, the reaction mixture was stirred with solvent that at a ratio of water/ether:chloroform is 4:1, then was extracted. Then, the organic phase was washed with 1N of HCl until the water phase became faint acid.

Then, the precipitates was washed with water, and after confirming neutral, the precipitates was washed with saturated common salt solution. After drying with magnesium sulfate, the solvent was removed therefrom with the evaporator to give the crystal of 1-acetyl-2-naphthoaldehyde was formed. Then, the crystal was recrystalized with ethanol anhydride to give the fall rate 50% of 1-acetyl-2-naphthoaldehyde(B) shown by the following formula 11.

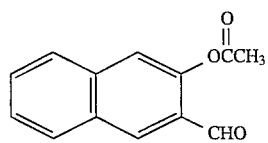

Then, 4 ml of tetrahydrofuran anhydride was added with 1.64 g of aforesaid 3,4-dimethetylbenzylphosphonium(A), then after stirring at 0° C. for 10 minutes, the mixture was stirred with 1.1 mol equivalent amount of sodium ethylate at 0° C. for 1 hours. The reaction mixture appeared red.

Then, 1.1 mol equivalent amount of said 1-acetyl-2-naphthoaldehyde (B) was slowly added to 4 ml of tetrahydrofuran anhydride. When red color of reaction solution disappeared, the reaction was stopped with saturated ammonium chloride, then 10% of hydrochloric acid was added to the reaction fluid so that the reaction fluid reached pH=4. Then, the residue was extracted with ether, and was washed with saturated common salt solution, and after drying with magnesium sulfate, the ether was removed therefrom with the evaporator to give the crystal.

The crystal was purified by silica gel column chromatography to give the fall rate 25% of 1-acetyl-2-alyl-[2'-(3,4-dimethylphenyl)]naphthalene(C) shown by the following formula 12.

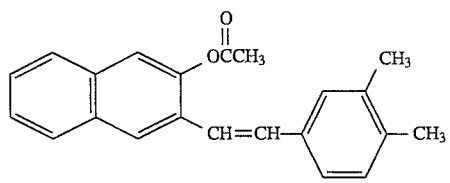

Then, 4 ml of ethanol was added to 150 mg of said 1-acetyl-2-alyl-[2'-(3,4-dimethylphenyl)]naphthalene(C), and excess calcium carbonate was added to the mixture, then the mixture was stirred at the room temperature for 1 hour. After confirming the disappearance of raw material with TLC, the reaction mixture was filtrated. Then the solvent was removed, and 5 cc of HCl of 1N was added to the mixture, then the mixture was extracted with chloroform, and was washed with saturated common salt solution, and was dried, and was filtrated. Then chloroform was removed from the mixture to give the fall rate 90% of 2-alyl-[2'-(3,4-dimethylphenyl)]naphthol(D) shown by the following formula 13.

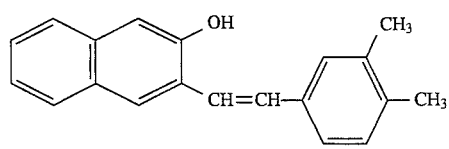

Then, 1 g of 2-alyl-[2'-(3,4-dimethylphenyl)]naphthol(D) was added to 8 ml of pyridine, then the mixture was stirred at 0° C. for 30 minutes, and was stirred with cooled oxy-phosphorus chloride (2.5 eq) at 0° C. for 4 hours. After this, the reaction was stopped with ice.

The reaction mixture was purified on a reverse phase silica gel column and then a normal phase silica gel column to give 2-aryl-[2'-(3,4-dimethylphenyl)]3-naphthol phosphatase shown by the following formula 14.

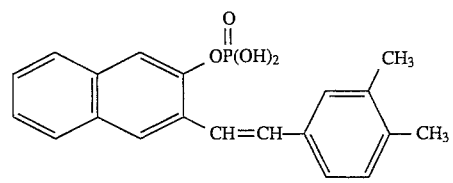

Detection test was conducted on this 2-aryl-[2'-(3,4-dimethylphenyl)]3-naphthol phosphatase.

EXAMPLE 2

According to the description of Enzyme Histochemistry, 5 g (0.027 mol) of 2-hydroxy-3-naphthoic acid, 3.8 g (0.023 mol) of 2-amino-4-methylbenzothiazole and 40 ml of xylene anhydride were stirred in a 100 ml NASU flusk provided with Graham condenser at 80° C. for 10 minutes.

Then, 0.01 mol of phosphorous trichloride was added thereto. The resulting mixture was refluxed for 2 hours. Thereafter, the reaction solution was decanted as in hot state to skim the supernatant fluid. After cooling the fluid at 4° C., it was subjected to filtration. The precipitates thus obtained was eluted with xylene and then water. Further, the precipitates was neutralized with 2% aqueous solution of sodium carbonate, and xylene was removed therefrom by boiling.

Then, the precipitates was rendered pH=9 with 2% aqueous solution of sodium carbonate, filtrated and cooled. The precipitates thus obtained was eluted with water. The precipitates was added to 3% HCl solution, heated, filtrated and then cooled. Then the precipitates was washed with hot water and dried.

Next, the precipitates were recrystallized to produce 3-hydroxy-2-naphthoamide (4 methylbenzothiasole) shown by the following formula 15.

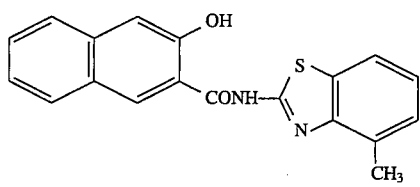

Formula 15

1 g of this naphtol derivative was dissolved in 8 ml of pylidine. After stirring this solution at 0° C. for 30 minutes, phosphous oxychloride (2.5 eq) cooled similarly was added thereto and stirred at 0° C. for 4 hours. Then, ice was added to the solution to terminate the reaction.

The reaction product thus obtained was purified by reverse phase silica gel column chromatography and then by normal phase silica gel column chromatography to produce 3-hydroxy-2-naphtthoamide(4-methylbenzothiasole)phosphate shown by the following formula 16.

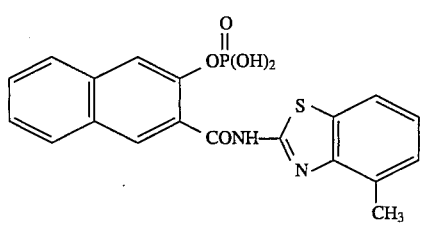

Formula 16

EXAMPLE 3

1 g ($2.95 \times 10^{-3}$ mol) of 2-hydroxy-3-naphthoic acid (2'-phenylanilide) was dissolved in 10 ml of chloroform anhydride. Next, 0.5 mol equivalent amount of phosphorus chloride($PCl_5$) was added to the solution and it was stirred at 40° C. for 2 hours. Then, chloroform was removed therefrom with the evaporator. The crystal of residue was dissolved in 10 ml of methanol anhydride, then 10 mol equivalent amount sodium methoxide was added to the solution fluid under ice cooled state. After the solution was stirred at 0° C. all night, the solution was purified by column chromatography to give 100 mg of 2-hydroxy-(2'-phenylanilide)-methyl-3-naphthoate.

Then, 3 ml of pyridine was dissolved with anhydride 2-hydroxy-(2'-phenylanilide)-methyl-3-naphthoate, after this the solution was stirred 0° C. for 30 minutes, and the 2.5 mol equivalent amount of oxy-phosphorus chloride was added to the solution fluid and the solution fluid was stirred 0° C. for 4 hours. After this, the ice was added to solution to terminate the reaction. Then, the solution fluid was purified by reverse silica gel column chromatography to give 30 mg of 2-hydroxy-(2'-phenylanilide)-methyl-3-naphthoate phosphate shown by the following formula 17.

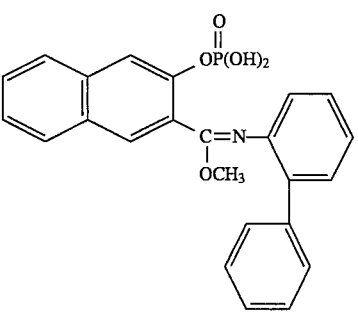

Formula 17

EXAMPLE 4

5 g of 2-amino-3-naphthol (0.0314 mol), 6.2 g of (0.0314 mol) and 40 ml of xylene anhydride was stirred in a 100 ml NASU flask at 80° C. for 10 minutes.

Then, in the same manner as Example 2, N-(2'-phenylbenzoic acid)-2-hydroxy-3-naphtylamine phosphate shown by the following formula 18 was given.

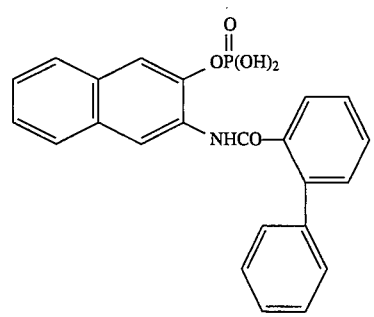

EXAMPLE 5

5 g of 2-amino-7-naphthol (0.0314 mol), 6.2 g of (0.0314 mol) and 40 ml of xylene anhydride were stirred in a 100 ml NASU flask at 80° for 10 minutes.

Then, in the same manner as Example 2, N-(4'-phenylbenzoic acid)-2-hydroxy-8-naphthylamine phosphate shown by the following formula 19 was given.

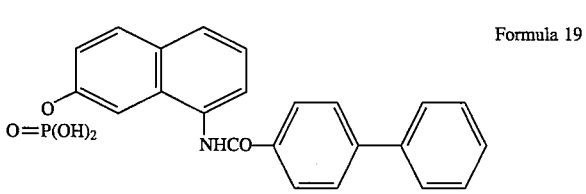

Formula 19

EXAMPLE 6

5 g of 2-hydroxy-6-naphthol (0.011 mol), 1.8 g of 2-phenyl aniline (0.011 mol) and 30 ml of xylene anhydride were stirred in a 100 ml NASU flask at 80° C. for 10 minutes.

Then, in the same manner as Example 2, 2-hydroxy-6-naphthoeacid (2'-phenylanilide) phosphate shown by the following formula 20 was given.

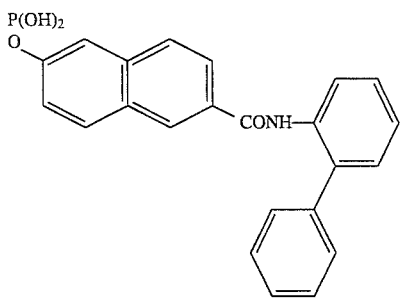

Detection test similar to Example 1 was conducted on each of the naphthol derivative phosphatate by the same method as in Example 1, i.e. spotting on the carrier filter for a specimen of nucleic acids.

The test results are shown in Table 1. As apparent from Table 1, the extremely small amount of DNA can be detected in high sensitivity.

TABLE 1

| EXAMPLE | Dig-labeled DNA (pg) | | | | | | |
|---|---|---|---|---|---|---|---|
| | 0 | 0.125 | 0.5 | 1 | 10 | 25 | 50 |
| 1 | − | ± | + | + | + | + | + |
| 2 | − | − | − | ± | + | + | + |
| 3 | − | − | − | − | − | − | + |
| 4 | − | − | − | − | − | − | + |
| 5 | − | − | − | ± | + | + | + |
| 6 | − | − | − | ± | + | + | + |

What is claimed is:

1. A method for detecting a nucleic acid in a sample, comprising:

a) contacting phosphatase with said sample, such that the nucleic acid to be detected in said sample binds to said phosphatase to form a modified phosphatase;

b) contacting said modified phosphatase with a naphthol derivative phosphate to form a fluorescent reaction product;

c) irradiating said fluorescent reaction product of said contacting step (b) with light, said light capable of eliciting fluorescence from said fluorescent reaction product; and d) detecting elicited fluorescence to detect said nucleic acid;

wherein:

said naphthol derivative phosphate has a formula selected from the group consisting of

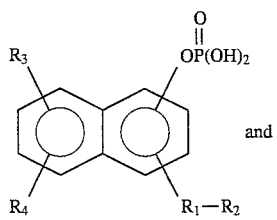

and

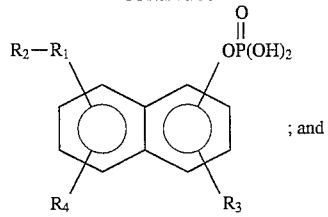

; and wherein:

$R_1$ is selected from the group consisting of amide, vinyl, $C_1$ to $C_3$ alkyl, ester, and $$-\underset{X}{\overset{|}{C}}=N-,$$

wherein X is alkoxide or phenoxide;

$R_2$ is selected from the group consisting of aryl, condensing aromatic, thio-aryl, alkyl, alkoxide, and phenoxide;

when $R_2$ is condensing aromatic, said condensing aromatic is selected from the group consisting of

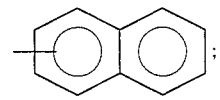

;

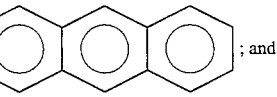

; and

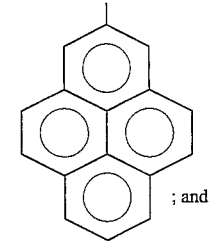

; and when $R_2$ is thioaryl, said thioaryl has the formula

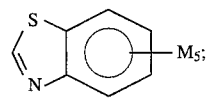

wherein $M_5$ is selected from the group consisting of hydrogen, $C_1$ to $C_2$ alkyl, alkoxide, cyano and aminoacetyl; and when $R_2$ is aryl, said aryl is represented by the formula

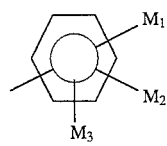

wherein $M_1$, $M_2$, and $M_3$ are independently selected from the group consisting of hydrogen, halogen, $C_1$ to $C_3$ alkyl, alkoxide, phenoxide, aminoacetyl, benzyl, aminophenyl, and cyano; and $R_3$ and $R_4$ are independently selected from the group consisting of hydrogen, halogen, alkyl, alkoxide, phenoxide, aminoacetyl, cyano, and ester.

2. The method of claim 1, wherein said naphthol derivative phosphate comprises the following formula:

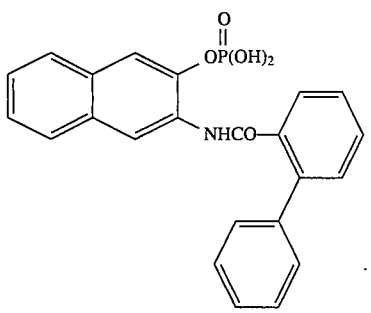

3. The method of claim 1, wherein said naphthol derivative phosphate comprises the following formula:

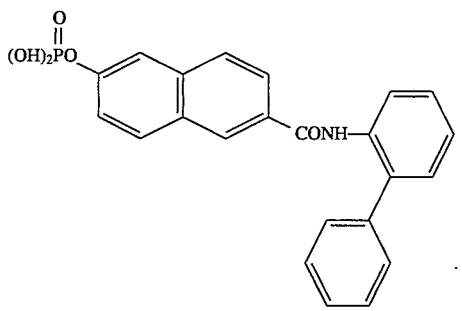

4. The method of claim 1, wherein said naphthol derivative phosphate comprises the following formula:

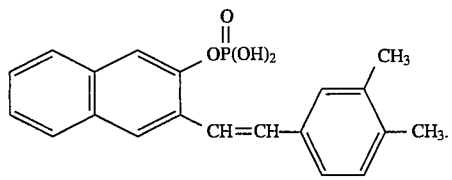

5. The method of claim 1, wherein said naphthol derivative phosphate comprises the following formula:

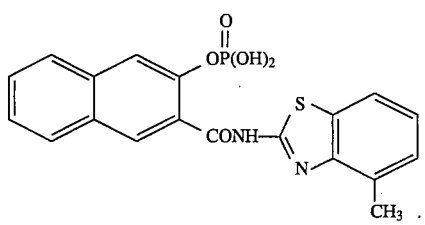

6. The method of claim 1, wherein said naphthol derivative phosphate comprises the following formula:

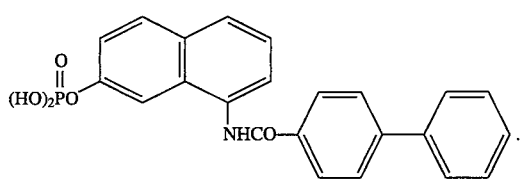

7. The method of claim 1, wherein said naphthol derivative phosphate comprises the following formula:

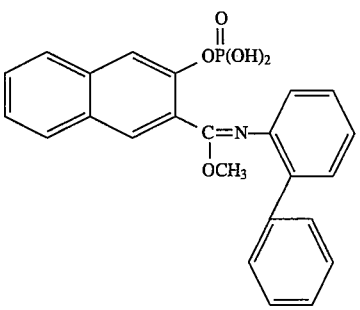

* * * * *